United States Patent
Kirane et al.

(10) Patent No.: US 11,768,193 B2
(45) Date of Patent: Sep. 26, 2023

(54) SYSTEM AND METHOD FOR CHARACTERIZING THE EQUIBIAXIAL COMPRESSIVE STRENGTH OF 2D WOVEN COMPOSITES

(71) Applicant: THE RESEARCH FOUNDATION FOR THE STATE UNIVERSITY OF NEW YORK, Albany, NY (US)

(72) Inventors: Kedar Kirane, Stony Brook, NY (US); Daniel Deland, Stony Brook, NY (US); Zongyan Zhang, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 17/786,713

(22) PCT Filed: Dec. 17, 2020

(86) PCT No.: PCT/US2020/065449
§ 371 (c)(1),
(2) Date: Jun. 17, 2022

(87) PCT Pub. No.: WO2021/127067
PCT Pub. Date: Jun. 24, 2021

(65) Prior Publication Data
US 2023/0044143 A1    Feb. 9, 2023

Related U.S. Application Data

(60) Provisional application No. 63/085,407, filed on Sep. 30, 2020, provisional application No. 62/951,674, filed on Dec. 20, 2019.

(51) Int. Cl.
*G01N 33/36* (2006.01)
*G01N 3/08* (2006.01)
(Continued)

(52) U.S. Cl.
CPC ............ *G01N 33/367* (2013.01); *G01N 3/08* (2013.01); *G01L 1/20* (2013.01); *G01L 1/205* (2013.01);
(Continued)

(58) Field of Classification Search
CPC .................. G01N 3/08; G01N 33/367; G01N 2203/0019; G01L 1/20; G01L 1/205;
(Continued)

(56) References Cited

U.S. PATENT DOCUMENTS

| | | | |
|---|---|---|---|
| 4,263,367 | A | 4/1981 | Prewo |
| 5,635,272 | A | 6/1997 | Bogetti et al. |

(Continued)

FOREIGN PATENT DOCUMENTS

| | | |
|---|---|---|
| CN | 1621803 A | 6/2005 |
| CN | 101389457 A | 3/2009 |

(Continued)

OTHER PUBLICATIONS

International Search Report dated Mar. 2, 2021 issued in PCT/US2020/065449.
(Continued)

*Primary Examiner* — Jonathan M Dunlap
(74) *Attorney, Agent, or Firm* — Scully, Scott, Murphy & Presser, P.C.

(57) ABSTRACT

A method and system for the characterization of equibiaxial compressive strength in 2D woven composites, such as carbon fiber reinforced laminate composites, is disclosed using induced biaxial flexure, the strain measurements from which are used to determine the equibiaxial compressive strength of the composite.

36 Claims, 2 Drawing Sheets

(51) Int. Cl.
   *G01L 1/20*    (2006.01)
   *G01L 1/22*    (2006.01)
   *G01L 5/161*   (2020.01)
   *G01L 5/1627*  (2020.01)
   *G01L 5/16*    (2020.01)

(52) U.S. Cl.
   CPC .............. *G01L 1/22* (2013.01); *G01L 5/16* (2013.01); *G01L 5/161* (2013.01); *G01L 5/1627* (2020.01); *G01N 2203/0019* (2013.01)

(58) Field of Classification Search
   CPC ... G01L 1/22; G01L 5/16; G01L 5/161; G01L 5/1627
   See application file for complete search history.

(56) References Cited

U.S. PATENT DOCUMENTS

| | | | |
|---|---|---|---|
| 6,487,902 | B1 | 12/2002 | Ghosh |
| 6,790,518 | B2 | 9/2004 | Grace et al. |
| 6,860,156 | B1 * | 3/2005 | Cavallaro ............... G01N 3/08 73/818 |
| 7,051,600 | B1 | 5/2006 | Cavallaro et al. |
| 7,204,160 | B1 | 4/2007 | Sadegh et al. |
| 2004/0082247 | A1 | 4/2004 | Desai et al. |
| 2005/0014430 | A1 | 1/2005 | Fredberg et al. |
| 2006/0222837 | A1 | 10/2006 | Kismarton |
| 2009/0068428 | A1 | 3/2009 | Shinoda et al. |
| 2009/0071196 | A1 | 3/2009 | Karayianni et al. |
| 2011/0079348 | A1 | 4/2011 | Tsuji et al. |
| 2014/0284855 | A1 | 9/2014 | Spiegel et al. |
| 2016/0349160 | A1 | 12/2016 | Esposito et al. |
| 2018/0067028 | A1 * | 3/2018 | Jelokhani Niaraki ... G01N 3/28 |
| 2019/0384878 | A1 | 12/2019 | Darcy et al. |
| 2020/0132575 | A1 * | 4/2020 | Meyer ..................... G01N 3/08 |

FOREIGN PATENT DOCUMENTS

| | | | |
|---|---|---|---|
| CN | 103970969 | A | 8/2014 |
| CN | 104880351 | A | 9/2015 |
| CN | 105980468 | A | 9/2016 |
| CN | 205910062 | U | 1/2017 |
| CN | 108896394 | A | 11/2018 |
| CN | 109883926 | A | 6/2019 |
| CN | 110160866 | A * | 8/2019 |
| DE | 69728874 | T2 | 9/2004 |
| DE | 102011119209 | A1 | 5/2013 |
| EP | 0536289 | B1 | 4/1995 |
| EP | 0905302 | A1 | 3/1999 |
| EP | 1816432 | A1 | 8/2007 |
| EP | 1966286 | B1 | 9/2009 |
| EP | 2821771 | B1 | 4/2019 |
| JP | H0872155 | A | 3/1996 |
| JP | H08209492 | A | 8/1996 |
| JP | H1044274 | A | 2/1998 |
| JP | 2002174572 | A | 6/2002 |
| JP | 2003254883 | A | 9/2003 |
| JP | 2004067487 | A | 3/2004 |
| JP | 3770844 | B2 | 4/2006 |
| JP | 2007056441 | A | 3/2007 |
| JP | 2007532019 | A | 11/2007 |
| JP | 2009517531 | A | 4/2009 |
| JP | 2013532075 | A | 8/2013 |
| JP | 2018039115 | A | 3/2018 |
| JP | 2019035603 | A | 3/2019 |
| JP | 2019531246 | A | 10/2019 |
| KR | 20140082687 | A | 7/2014 |
| WO | 1993018912 | A1 | 9/1993 |
| WO | 1996014455 | A1 | 5/1996 |
| WO | 2003053679 | A1 | 7/2003 |
| WO | 2005065942 | A1 | 7/2005 |
| WO | 2007099825 | A1 | 9/2007 |
| WO | WO-2010082977 | A1 * | 7/2010 ............... G01N 3/20 |
| WO | 2013101309 | A1 | 7/2013 |
| WO | 2018031596 | A2 | 2/2018 |

OTHER PUBLICATIONS

Written Opinion dated Mar. 2, 2021 issued in PCT/US2020/065449.
English-language translation of Japanese Notice of Reasons for Rejection dated Nov. 21, 2022, received in a corresponding foreign application, 2 pages.
English-language translation of Chinese Office Action and Search Report dated Jan. 20, 2023, received in a corresponding foreign application, 15 pages.
Tsangarakis, N., et al. "Blaxial Flexing of a Fiber-Reinforced Aluminum Composite", U.S. Army Materials Technology Laboratory, Jul. 1989, 23 pages.
Pick, B., et al. "A critical view on biaxial and shortbeam uniaxial flexural strength tests applied to resin composites using Weibull, fractographic and finite element analyses", Dental Materials, Sep. 2009, pp. 83-90, 26.
Kim., J., et al., "Investigating the flexural resistance of fiber reinforced cementitious composites under biaxial condition", Composite Structures, Dec. 2014, pp. 198-208 122.
Kalluri, S., et al., "Multiaxial Fatigue and Deformation: Testing and Prediction", ASTM stock No. STP 1387, 2018, 444 pages.
Carrasco-Pena, A., et al., "Design and development of ring-on-ring jig for biaxial strength testing of brittle ceramic composite materials: ZrB2-30wt-%SiB6", Advances in Applied Ceramics, Apr. 2019, pp. 159-168, vol. 118, No. 4.
Zi, G., et al., "A novel indirect tensile test method to measure the biaxial tensile strength of concretes and other quasibrittle materials", Cement and Concrete Research, Feb. 2008, pp. 751-756, 38.

* cited by examiner

SYSTEM AND METHOD FOR CHARACTERIZING THE EQUIBIAXIAL COMPRESSIVE STRENGTH OF 2D WOVEN COMPOSITES

This application claims priority under 35 U.S.C. § 119 to U.S. Provisional Patent Application Ser. No. 62/951,674, filed Dec. 20, 2019, and U.S. Ser. No. 63/085,407, filed Sep. 30, 2020, the entire contents of each of which are incorporated herein by reference.

FIELD

The disclosure relates to a method for characterizing the equibiaxial compressive strength of 2D woven composites including, without limitation, carbon fiber reinforced composites and the like, and a system for same.

BACKGROUND

Thin composite structures used in a wide variety of engineering applications, such as aircraft wings, wind turbine blades, belts and plies in automobile tires, pressure vessels used for storage/transport etc. For reliable operation and efficient design of these thin engineering structures, it is essential to characterize and understand their failure behavior under biaxial flexure, among other stress states. While certain research into the biaxial strength of fiber reinforced composites exists, studies involving biaxial flexural failure of plates are less common. Several testing standards exist for isotropic brittle materials, but no such standard exists for anisotropic composite materials. A common method for biaxial flexure testing of isotropic materials involves supporting a disc or plate shaped specimen on a circular ring and applying an out of plane loading at or near the center. The out of plane loading is applied either through a ball (ball on ring, BOR), or by applying uniform pressure (pressure on ring, POR) or via a smaller circular ring (ring on ring, ROR). Another test method employs, in lieu of a loading ring, a point load applied on the top with the disk is supported on three pivots along the perimeter; this is a standard test for concrete (ASTM C1550 test) and also dental ceramics (ISO 6872). In this test, the induced stress field is threefold symmetric and equibiaxial only at the load point.

The ring on ring (ROR) bending test is simple to conduct and is subject of an ASTM standard test for the measurement of the equibiaxial tensile strength of ceramics (ASTM C1499). The loading produced by the ROR set up is analogous to the four-point bending test of a beam in 2D. In other words, each diametrical section of the specimen may be viewed as a beam undergoing four point bending. Thus, the region of the disk or plate shaped specimen within the loading ring undergoes pure bending. For isotropic materials the elastic-stress distribution in the region within the loading ring is axisymmetric. This testing procedure has been applied to ceramics that exhibit macroscopically isotropic behavior and are homogeneous in structure. The method has also been extended to glass and recently also to concrete.

Plate bending tests have been applied mainly to isotropic brittle materials, but some studies on anisotropic composites can be found (though not necessarily with the ROR test). In some early works, the behavior of fiber glass-reinforced polyester (FRP) and FRP-polyurethane foam composites was studied to evaluate these materials for possible use as pavement materials. Uniaxial flexure, tension and biaxial flexure tests have been performed under monotonic and cyclic loading. These biaxial flexure tests involved a circular plate specimen subjected to a central lateral load with an all-round clamped support. The results of the uniaxial tests were found to be in good agreement with the biaxial tests. Biaxial flexure of silicon carbide continuous fiber reinforced aluminium composite is also known, employing an ROR test set up and studied the failure mechanism. It was found that fiber fracture and matrix cracks both occurred under monotonic loading, whereas under cyclic flexing, fiber fracture was the major failure mechanism. The response of a cross ply carbon fiber resin composite has also been analyzed under biaxial flexural using disk specimens, with focus on comparing failure mode under monotonic and cyclic loading. Additional applications may be found for dental resin composites, fiber reinforced cementitious composites, and ceramic composites.

Despite these examples, plate bending tests are not common for anisotropic fiber reinforced polymer matrix composites. A speculated reason for this is the existence of edge effects which cause failure to initiate at the edges rather than the center. However, this is not consistently true. Consequently, there is a need for a simple, reliable, cost effective, and repeatable test to characterize the equibixial compressive strength of 2D woven fabric composites.

SUMMARY

On one aspect, the disclosure is directed to a method for determining equibiaxial compressive strength in a 2D woven composite, such as a carbon fiber reinforced laminate, where the 2D woven composite comprises at least a first set of fibers disposed in a first fiber direction and a second set of fibers disposed in a second fiber direction, the first and second set of fibers interlaced at an angle, e.g. at a right angle to each other. The method comprises applying an out-of-plane uniaxial load, e.g. a monotonic load, to the 2D woven composite specimen to induce a biaxial flexure in the 2D woven composite specimen; obtaining strain measurements, e.g. by two or more strain gauges disposed along the first fiber direction and the second fiber direction of the 2D woven composite specimen that has been induced to have the biaxial flexure; and determining the equibiaxial compressive strength of the 2D woven composite specimen from the stresses calculated from the strain measurements obtained along the first fiber direction and along the second fiber direction when at least one visible crack appears in the top surface of the 2D woven composite specimen and/or when the measurements from strain gauges no longer overlap but diverge. In another aspect, the disclosure is directed to a system for determining the equibiaxial strength of a 2D woven composite.

DETAILED DESCRIPTION

In the following detailed description of certain embodiments of the disclosure, explanation about related functions or constructions known in the art are omitted for the sake of clearness in understanding the concept of the invention to avoid obscuring the invention with unnecessary detail.

Embodiments of the system and method described herein provide a reliable measurement of the equibiaxial compressive strength of 2D woven composites by application of a uniaxial load, with using a specimen geometry and test set up. The testing method exemplified for this purpose is the ring on ring (ROR) flexure test. In this test, the biaxial strength is measured by subjecting un-notched circular disks or un-notched square plates to a monotonic, out of plane load at the center. This induces biaxial flexure of the specimen and converts a uniaxial load into a biaxial state of stress. This test set up is inexpensive and the specimen geometry is simple. It also does not require any expensive specimen grips and can be conducted in a standard universal testing machine (i.e. does not require a separate load frame, load cells etc). As further described herein, numerical stress analysis and experimental measurements using this method are provided. The system and method are stable, reliable, repeatable and potentially applicable to a variety of fiber-reinforced composites. Characterization of the equibiaxial strength of composites is necessary for accurate estimates of the load capacity of structures subjected to biaxial compression, critically because composites are usually weaker in compression.

In one embodiment, the disclosure provides a method for determining equibiaxial compressive strength in a 2D woven composite. In one practice, the method comprises providing a 2D woven composite specimen where the specimen comprises at least a first set of fibers disposed in a first fiber direction and a second set of fibers disposed in a second fiber direction, the first and second set of fibers interlaced at an angle, e.g. the first set of fibers is interlaced orthogonally to the second set of fibers. In one practice, the first and the second set of fibers correspond respectively to the warp and weft yarns in a woven composite. The first and second set of fibers can be interlaced in a plain weave pattern, a twill pattern, a satin pattern, a basket weave pattern, or a rib pattern. The first and second set of fibers can also comprise a knitted composite.

Figure 1:
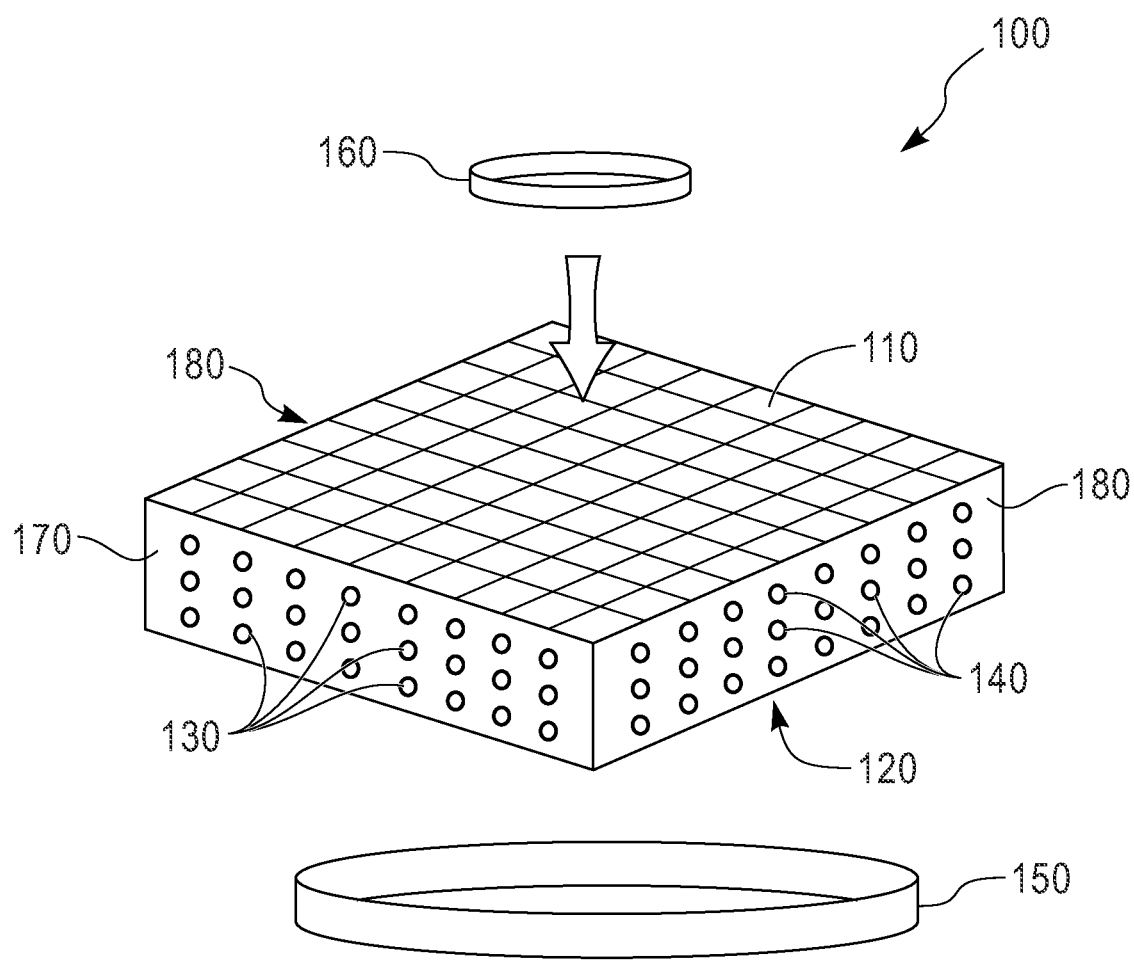
FIG. 1 is an exploded perspective view of a general scheme showing the geometry set up of an embodiment of the method of the disclosure.

As seen in the non-limiting embodiment of FIG. 1, 2D woven composite specimen 100 comprises a top surface 110 and a bottom surface 120. The 2D woven composite specimen can be in the shape of an un-notched circular disk, or an un-notched square plate (as depicted in FIG. 1), and comprises a first set of fibers 130 (partly shown) disposed in a first fiber direction, as shown, the direction which runs the length of and parallel to side 180 (the first fiber direction), and s second set of fibers 140 disposed in a second fiber direction, as shown the direction which runs the length of and parallel to side 170 (the second fiber direction), which set of second fibers are interlaced at an angle, shown as orthogonally, with the first set of fibers 130. As depicted, the 2D woven composite can be a laminate comprising multiple layers, for example and without limitation, 8 to 12 layers, e.g. 10 layers, although more or less layers are contemplated (three layers being shown for convenience), wherein the first set of fibers 130 in one layer is aligned with the first set of fibers in the other layers above and below, and the second set of fiber in one layer is aligned with the second set of fibers in the other layers above and below. Bottom surface 120 is supported on support ring 150 and an out-of-plane uniaxial load (shown by the arrow), which in one practice is a monotonic load, is applied to the center of the top surface 110 by loading ring 160 which is concentric with support ring 150 to induce a biaxial flexure in the 2D woven composite specimen. Support ring 150 and loading ring 160 can each be circular with loading ring 160 being concentric to support ring 150, e.g. support ring 150 has a diameter 3 to 5 times greater than the diameter of loading ring 160; and both rings are comprised of a material suitably rigid to withstand the forces applied, e.g. metals including steel. The 2D woven composite specimen has a thickness sufficient to permit inducement of biaxial flexure, for example, without limitation, 2 mm to 3 mm. In one practice, the first set of fibers and the second set of fibers are embedded in a matrix, which can comprise one or more polymers such as a thermoplastic material or a thermoset material, e.g. a vinyl ester or an epoxy resin, respectively. Without limitation, the 2D woven composite specimen can comprise an orthotropic fiber-reinforced composite comprising fibers selected from carbon fibers, glass fibers, polymeric fibers, and combinations of the foregoing, and a matrix selected from an epoxy or a vinyl ester.

In one embodiment, the 2D woven composite specimen comprises a first fiber elastic modulus as measured along the first fiber direction, and a second fiber elastic modulus as measured along the second fiber direction; optionally at least one additional elastic modulus measured along a direction other than the first fiber direction or second fiber direction is present wherein the first fiber elastic modulus and the second fiber elastic modulus are each independently greater than the at least one additional elastic modulus. When the first set of fibers and the second set of fibers are embedded in a matrix, the matrix itself comprises a matrix elastic modulus, and the first fiber elastic modulus and the second fiber elastic modulus are each individually greater than the matrix modulus. For example, each of the first fiber elastic modulus and the second fiber elastic modulus are individually at least 5 times greater than the matrix modulus. In another practice, the 2D woven composite specimen comprises a tensile strength and a uniaxial compressive strength, wherein the tensile strength is greater than the unaxial compressive strength. Elastic modulus (also known as Young's modulus) for the composite comprising the first and second set of fibers and the matrix, and the tensile strength of the composite is obtained by means conventionally known in the art, such as by application of the well known test standard ASTM D3039/D3039M-14, Standard Test Method for Tensile Properties of Polymer Martrix Composite Materials, ASTM International, West Conshohocken Pa., or is obtained from the manufacturer of commercially available composites. Compressive strength (uniaxial) is obtained by means conventionally known in the art, such as by application of the well known test standard ASTM D6641/D6641M-16e1, Standard Test Method for Compressive Properties of Polymer Matrix Composite Materials Using a Combined Loading Compression (CLC) Test Fixture, ASTM International, West Conshohocken Pa. or is obtained from the manufacturer of commercially available composites.

Figure 2:
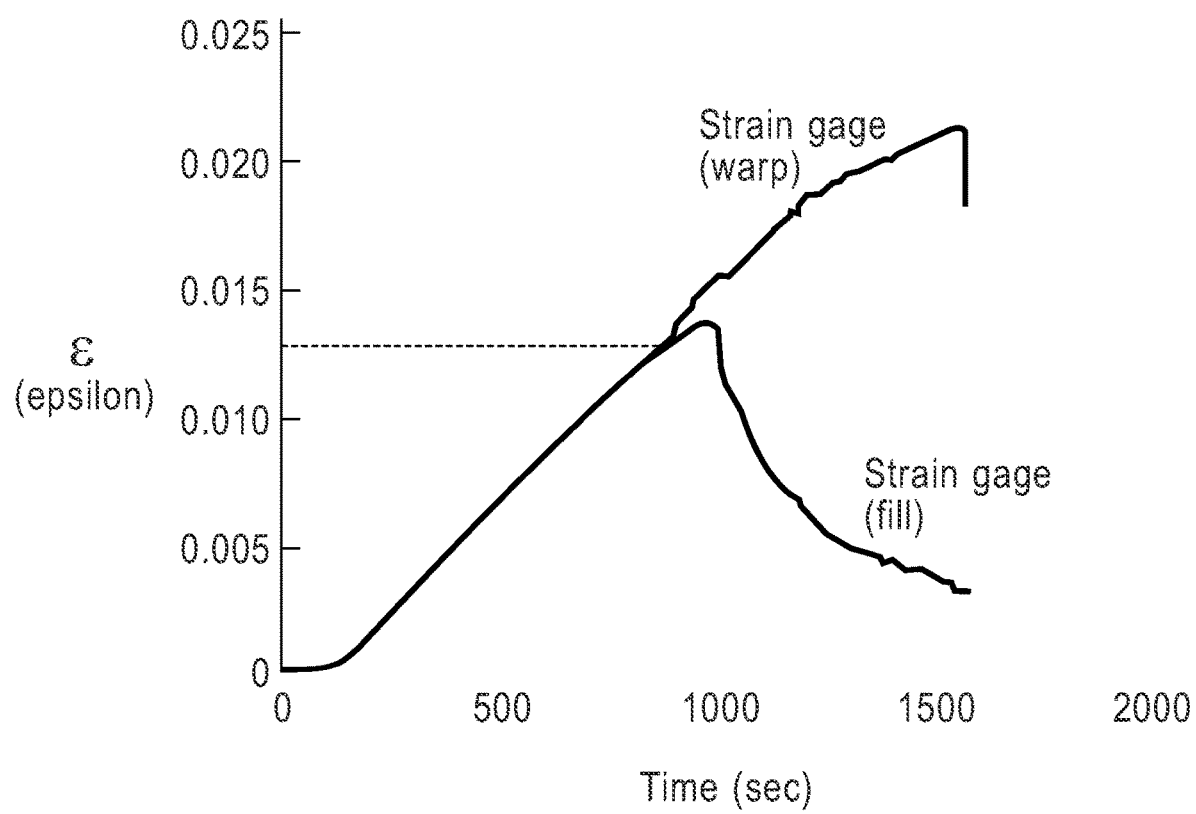
FIG. 2 is a graphical depiction of measured strains in a 2D woven composite according to the exemplified embodiment of the disclosure.

In one practice of the method, strain measurements are obtained along the first fiber direction and the second fiber direction of the 2D woven composite specimen induced to have the biaxial flexure. The strain measurements can be obtained in situ on the side of the 2D woven composite specimen opposite the side to which the out-of-plane uniaxial force is applied, e.g. the strain measurements can be obtained on the bottom surface 120 of the 2D woven composite specimen 100 when the out-of-plane uniaxial force is applied to top surface 110. Strain measurements can be gotten from commercially available strain gauges which can be attached to the bottom surface 120, such as without limitation, at or near the center of the bottom surface 120. In one practice, two strain gauges are used, where a first strain measurement is obtained from first strain gauge that is operatively connected as known in the art to the bottom surface 120 in a configuration that is parallel to the first fiber direction (fibers 130), and a second strain measurement is obtained from a second strain gauge that is operatively connected as known in the art to the bottom surface 120 in a configuration that is parallel to the second fiber direction (fibers 140). In one embodiment, the first and second strain gauges are each individually attached at and/or near the center of 2D woven composite specimen. In one practice a monotonic out-of-plane uniaxial load is applied until failure of the composite, that is when the top surface 110 of the 2D woven composite specimen develops at least one visible crack, or when the strain measurement along the first fiber direction and the strain measurement along the second fiber direction diverge, as shown in FIG. 2 and as exemplified below. The equibiaxial compressive strength can be determined from stresses that are calculated from the strain measurements obtained along the first fiber direction and along the second fiber direction at the point of visible cracking or strain gauge divergence. In one practice, the measurement of strain on the bottom surface is used to yield the strains on the top surface, which can in turn yield the state of stress the stress calculations from which characterize the biaxial flexural strength, Fbf, of the composite via the following equation (1):

$$F_{bf} = Q_{11} \varepsilon_c + Q_{12} \varepsilon_c \quad (1)$$

where Q11 and Q12 are defined in equations (2) and (3), and at $\varepsilon_c$ is the strain gauge measurement at failure, i.e. when at least one visible crack develops in the top surface of the 2D woven composite specimen or when the measurements of the first strain gauge and the second strain gauge diverge, whichever comes first.

$$Q_{11} = \frac{E_1}{1 - V_{12} V_{21}} \quad (2)$$

$$Q_{12} = \frac{V_{21} E_1}{1 - V_{12} V_{21}} = \frac{V_{12} E_2}{1 - V_{12} V_{21}} \quad (3)$$

Where $E_1$ is the first fiber elastic modulus measured along the first fiber direction by e.g. ASTM D3039/D3039M-14 or other means known in the art, and $E_2$ is the second fiber elastic modulus measured along the second fiber direction by e.g. ASTM D3039/D3039M-14 or other means known; $V_{12}$ is the in-plane Poisson's ratio for the first (pull) and second (contraction) fiber directions and $V_{21}$ is the in-plane Poisson's ratio for the second (pull) and first (contraction) fiber directions as measured by ASTM E132-04, (2014) Standard Test Method for Poisson's Ration at Room Temperature, ASTM International, West Conshohocken Pa.

For Tests 1 and 2 conducted in the example, the values of $E_1$, $E_2$, $V_{12}$, and $V_{21}$ were:
$E_1$=42110.53 MPa
$E_2$=42110.53 MPa
$V_{12}$=$V_{21}$=0.12

From these, $Q_{11}$ and $Q_{12}$ were calculated from equations (2) and (3) to be:
$Q_{11}$=47275.78 MPa
$Q_{12}$=5127.094 MPa For Tests 1 and 2, the value of $\varepsilon_c$ was measured by the method of the disclosure as:
$\varepsilon_c$ (for test 1) at point of strain divergence from FIG. 2=0.014
$\varepsilon_c$ (for test 2, graph not shown but similar to FIG. 2)=0.013

From equation (1), the equibixial compressive strength for the Test 1 and 2 woven composite were:
Test 1: $F_{bf}$=670 MPa
Test 2: $F_{bf}$=622 MPa Thus, an accurate characterization of the equibiaxial compressive strength for 2D woven composites is ascertainable using in situ measurement of the principal strains, i.e. here, strains in the first and second fiber direction, and the knowledge of the elastic moduli and the in-plane Poisson's ratios.

EXAMPLE

The following example is illustrative of the disclosure and not limiting to same.

Ring on Ring testing of a 2D woven composite specimen:

The ring on ring bending test (ROR) set up in this example was designed using the well known ASTM C1499 standard for the equibiaxial flexure testing of ceramics. The loading ring had a diameter of 20 mm and radius of the cross section of the loading ring was 5 mm. The support ring had a diameter of 100 mm and the radius of the cross section of the support ring was 10 mm. Both rings were made of steel. While it is common to test a circular ceramic disk, for composites, it is much easier to make a square shaped plate, since it is typically cut out of a larger plate laminate. An un-notched square shaped composite specimen of 105 mm×105 mm size was employed.

Fabrication of the 2D Woven Composite Specimen:

The woven composite plate specimens for the ring on ring bending tests were prepared via the vacuum assisted resin infusion technique. The composite was made from system 2000 epoxy resin with a 120 minute pot life and 3K, 2×2 plain weave carbon fiber woven fabric, both purchased from Fibre Glast Development Corp. The epoxy resin was mixed with hardener, at a resin-to-hardener mix ratio of 100:27 as specified by the supplier. Ten layers of the woven carbon fabric, cut to desired dimension were laid up on a flat panel and then sealed in a vacuum bag. The layers were aligned so as to produce a uniform lay up, i.e. [0°]$_{10}$. The vacuum bag was then connected to the resin pot on one end, and to a General Electric ⅓ hp vacuum pump at the other end. The vacuum pressure was maintained between 25 and 30 inches Hg which ensured a uniform infusion of the resin in the fabric layers. Upon infusion the system was left to dry for 24 hours before being unpacked from the vacuum bag. The final cured composite laminate plate with ten layers with a total thickness of 3.2 mm was pulled from the vacuum bag and was cut into the desired 105 mm×105 mm specimen sizes for testing.

Test Description:

For the ROR bending tests, square plates were cut of size 105 mm×105 mm. These were cut such that the warp and weft yarns were parallel to the sides of the square. The composite plate specimens were then tested under biaxial flexure using the steel support and loading rings. A small layer of mattress foam was interposed between the loading ring and the composite to prevent indentation and ensure an even distribution of the applied loading. The test was conducted in displacement control at a rate of 0.5 mm/min. In all four ring on ring bending tests were conducted. Two tests, Tests 1 and 2, performed on 2D woven composites specimens as prepared according to the example are reported herein.

Discussion:

Two ring-on-ring bending tests (Tests 1 and 2) were conducted until failure. The machine recorded the load and displacement. After a certain point, the load reached its peak and then dropped significantly, though not to zero. It was seen that in both runs, failure initiated and propagated on the top surface of the woven composite, not on the bottom surface, as occurs for ceramics or the previously tested epoxy. Tests 1 and 2 were conducted by using strain gauges. Since fracturing occurred on the top surface, it would be desirable to measure top surface strains, however that was not possible due to interference with the loading ring, thus two strain gauges were attached on the bottom surface of the composite, at the center of the plate. Each strain gauge was parallel to one of the two principal fiber directions, thereby measuring both principal strains $\epsilon_1$ and $\epsilon_2$, that is strains in the first and second fiber directions. The strain gauges were obtained from Omega Engineering, were pre-wired and were linear, X-Y Planar Rosette type. They had a maximum strain capacity of 50,000 µstrain and a grid size of 2 mm×3 mm. Slots of suitable dimension were also cut on the support ring, in order to let the strain gauge wires out for connection to the strain gauge recorder. In these two tests using the strain gauges, failure occurred progressively on the top surface of the composite.

The strain gauge measurements for Test 1 (y-axis, $\epsilon$) is shown in FIG. 2. As shown in FIG. 2, it is seen that $\epsilon_1 = \epsilon_2$ (the strain gauge measurements in the first and second fiber directions respectively) which indicates an equibiaxial tensile state of strains on the bottom surface of the composite. Thus, under pure bending, the strain state on the top surface of the composite would also be equibiaxial, but compressive. Notably, at FIG. 2, at approximately $\epsilon_c = 0.014$ at failure on the top surface was observed; in this instance, the strain gauge measurements in the first and second fiber direction, $\epsilon_1$ and $\epsilon_2$, diverge ($\epsilon_c$, the strain measurement at failure).

The mechanical load displacement behavior of woven composite plates under this test was different from other brittle materials (ceramics, concrete, glass, epoxy etc). Firstly, failure occurred on the top surface, which is under biaxial compression. This indicated that the composite is weaker under biaxial compression than biaxial tension. This is consistent with the broader understanding on compression failures of composites. In contrast, for other brittle materials failure occurs on the bottom surface, triggered by biaxial tension. Secondly, for the 2D woven composite a sharp well-defined peak is not observed due to a more progressive damage accumulation. The small pre-peak load drops indicate onset of damage. During these load drops the strain gauge readings (on the bottom surface) still showed perfect equi-biaxiality. This verified that the damage is on the top side of the specimen. And at onset, the damage did not disrupt the strain field on the bottom side. This can be attributed to the layered structure of the composite, where the interface between layers tends to decelerate the damage. Thirdly, even beyond the peak load, the failure was not catastrophic, i.e. the load did not drop fully to zero. This was due to fracturing being confined to only to the top one or two layers. This is again because of the heterogeneous layered arrangement of the composite. However, when the load shows a large drop, the strain gauge readings in the first and second fiber directions diverged, indicating that damage was significant enough to disrupt the elastic stress/strain field all the way to the bottom. In other brittle materials the failure is catastrophic with the load dropping to zero at failure. For 2D woven composites, the failure was seen to occur by the formation of radial kink bands on the top surface, which initiate at the center of the specimen, and propagate towards the edges. These were mostly confined to the top layer and no through-thickness failures were observed. This pattern is similar to that observed for ceramics/concrete (and even epoxy as shown earlier) consisting of several radial tensile fractures.

Results of Test 1 and Test 2:

For Tests 1 and 2 conducted in the example, the values of $E_1$, $E_2$, $V_{12}$, and $V_{21}$ obtained as described herein were:
$E_1 = 42110.53$ MPa
$E_2 = 42110.53$ MPa
$V_{12} = V_{21} = 0.12$ From these, $Q_{11}$ and $Q_{12}$ were calculated from equations (2) and (3) to be:
$Q_{11} = 47275.78$ MPa
$Q_{12} = 5127.094$ MPa For Tests 1 and 2, the value of $\epsilon_c$ was measured by the method of the disclosure as:
$\epsilon_c$ (for test 1) at point of strain divergence from FIG. 2 = 0.014
$\epsilon_c$ (for test 2, graph not shown but similar to FIG. 2) = 0.013

From equation (1), the equibixial compressive strength for the Test 1 and 2 woven composite were:
Test 1: $F_{bf} = 670$ MPa
Test 2: $F_{bf} = 622$ MPa Thus, an accurate characterization of the equibiaxial compressive strength for 2D woven composites is ascertainable using in situ measurement of the principal strains, i.e. here, strains in the first and second fiber direction, and the knowledge of the elastic modulii and the in-plane Poisson's ratios.

While the disclosure has been shown and described with reference to certain embodiments, it will be understood by those skilled in the art that various changes in from and details may be made therein without departing from the spirit and scope of the present invention and equivalents thereof.

What is claimed is:

1. A method for determining equibiaxial compressive strength in a 2D woven composite comprising:
   providing a 2D woven composite specimen comprising at least a first set of fibers disposed in a first fiber direction and a second set of fibers disposed in a second fiber direction, the first and second set of fibers interlaced at an angle;
   applying an out-of-plane uniaxial load to the 2D woven composite specimen to induce a biaxial flexure in the 2D woven composite specimen;
   obtaining strain measurements along the first fiber direction and the second fiber direction of the 2D woven composite specimen induced to have the biaxial flexure; and
   determining the equibiaxial compressive strength of the 2D woven composite specimen from the strain measurements obtained.

2. The method of claim 1 wherein the equibiaxial compressive strength is determined from stresses calculated from the strain measurements obtained along the first fiber direction and along the second fiber direction.

3. The method of claim 1 wherein the 2D woven composite specimen comprises a first fiber elastic modulus measured along the first fiber direction, a second fiber elastic modulus measured along the second fiber direction, and optionally at least one additional elastic modulus measured along a direction other than the first fiber direction or second fiber direction and wherein the first fiber elastic modulus and the second fiber elastic modulus are each independently greater than the at least one additional elastic modulus.

4. The method of claim 3 wherein the first set of fibers and the second set of fibers are embedded in a matrix, the matrix comprising a matrix elastic modulus, and wherein the first fiber elastic modulus and the second fiber elastic modulus are each individually greater than the matrix modulus.

5. The method of claim 4 wherein each of the first fiber elastic modulus and the second fiber elastic modulus are each individually at least 5 times greater than the matrix modulus.

6. The method of claim 4 wherein the matrix comprises a thermoplastic material or a thermoset material.

7. The method of claim 6 wherein the matrix comprises an epoxy or a vinyl ester.

8. The method of claim 1 wherein the 2D woven composite specimen comprises a tensile strength and a uniaxial compressive strength, wherein the tensile strength is greater than the unaxial compressive strength.

9. The method of claim 1 wherein the first set of fibers and the second set of fibers are interlaced at an angle of 90°.

10. The method of claim 1 wherein the first and second set of fibers are interlaced in a plain weave pattern, a twill pattern, a satin pattern, a basket weave pattern, or a rib pattern.

11. The method of claim 1 wherein the 2D woven composite specimen comprises a laminate structure of multiple layers wherein the first fiber direction in each layer is the same and the second fiber direction in each layer is the same.

12. The method of claim 11 wherein the laminate structure comprises 8 to 12 layers.

13. The method of claim 11 wherein the laminate structure has a thickness of 2 mm to 3 mm.

14. The method of claim 1 wherein the out-of-plane uniaxial load is monotonic.

15. The method of claim 14 wherein the out-of-plane uniaxial load is applied at the center of the 2D woven composite specimen.

16. The method of claim 1 wherein the strain measurements are obtained in situ on the side of the 2D woven composite specimen opposite the side to which the out-of-plane uniaxial force is applied.

17. The method of claim 1 wherein the out-of-plane uniaxial load is applied until the top surface of the woven composite specimen develops at least one visible crack or when the strain measurement along the first fiber direction and the strain measurement along the second fiber direction diverge.

18. The method of claim 17 wherein the equibiaxial compressive strength of the woven composite specimen is determined from stresses calculated from the strain measurements obtained along the first fiber direction and the second fiber direction obtained when the top surface of the woven composite specimen develops the at least one visible crack or when the strain measurement along the first fiber direction and the strain measurement along the second fiber direction diverge.

19. The method of claim 1 wherein the 2D woven composite specimen is held on a support ring and the out-of-plane uniaxial load is applied by a loading ring that is concentric to the support ring.

20. The method of claim 19 wherein the support ring is comprised of steel.

21. The method of claim 19 wherein the support ring has a diameter that is 3 to 5 times greater than the diameter of the loading ring.

22. The method of claim 1 wherein the 2D woven composite specimen is in the shape of an un-notched circular disk, or an un-notched square plate.

23. The method of claim 1 wherein the 2D woven composite specimen comprises an orthotropic fiber-reinforced composite comprising fibers selected from carbon fibers, glass fibers, polymeric fibers, and combinations of the foregoing, and a matrix selected from an epoxy or a vinyl ester.

24. A method for method for determining equibiaxial compressive strength in a woven composite comprising:
  (i) providing a 2D woven composite specimen on a support ring, the 2D woven composite specimen comprising multiple layers and comprising:
    a top surface and a bottom surface, the bottom surface of the 2D woven composite specimen in contact with the support ring,
    a first set of fibers disposed in a first fiber direction and a second set of fibers disposed in a second fiber direction, the first set of fibers and the second set of fibers interlaced at an angle of 90°,
    a first fiber elastic modulus measured along the first fiber direction, a second fiber elastic modulus measured along the second fiber direction, and optionally at least one additional elastic modulus measured along a direction other than the first fiber direction or second fiber direction, wherein the first fiber elastic modulus and the second fiber elastic modulus are each independently greater than the at least one additional elastic modulus, and wherein the 2D woven composite specimen comprises a tensile strength and a uniaxial compressive strength, the tensile strength greater than the unaxial compressive strength, and
    a matrix in which the first set of fibers and the second set of fibers are embedded, the matrix comprising a matrix elastic modulus, the first fiber elastic modulus and the second fiber elastic modulus each individually greater than the matrix modulus, the bottom surface of the 2D woven composite specimen in contact with the support ring;
  (ii) measuring a first strain with a first strain gauge operatively connected to the bottom surface in a configuration that is parallel to the first fiber direction, and measuring a second strain with a second strain gauge operatively connected to the bottom surface in a configuration that is parallel to the second fiber direction;
  (iii) applying an out-of-plane uniaxial load to the center of the 2D woven composite specimen by contacting a loading ring to the to the top surface of the woven composite specimen under montonic force to induce biaxial flexure in the 2D woven composite until at least a portion of the top surface of the woven composite specimen develops at least one visible crack or until the first and second strain measurements diverge, the loading ring having a diameter less than the diameter of the support ring and disposed concentric to the support ring;
  (iv) obtaining strain measurements on the 2D woven composite specimen from the first and second strain gauges during step (iii); and
  (v) determining the equibiaxial compressive strength of the woven composite specimen from stresses calculated from the strain measurements obtained along the first fiber direction and along the second fiber direction.

25. The method of claim 24 wherein the support ring has a diameter that is 3 to 5 times greater than the diameter of the loading ring.

26. The method of claim 24 wherein the 2D woven composite specimen is in the shape of an un-notched circular disk, or an un-notched square plate.

27. The method of claim 24 wherein the first set of fibers and the second set of fibers are interlaced in a plain weave pattern, a twill pattern, a satin pattern, a basket weave pattern, or a rib pattern.

28. The method of claim 24 wherein the 2D woven composite specimen comprises a laminate structure of multiple layers wherein the first fiber direction in each layer is the same and the second fiber direction in each layer is the same.

29. The method of claim 28 wherein the laminate structure comprises 8 to 12 layers.

30. The method of claim 29 wherein the laminate structure has a thickness of 2 mm to 3 mm.

31. The method of claim 24 wherein the matrix comprises a thermoplastic material or a thermoset material.

32. The method of claim 31 wherein the matrix comprises an epoxy or a vinyl ester.

33. The method of claim 24 wherein a indentation protective insert material is interposed between the top surface of the woven composite specimen and the loading ring.

34. The method of claim 33 wherein the indentation protective insert is comprised of foam or fluoropolymer or both.

35. A system for determining equibiaxial compressive strength in a woven composite comprising:

a support ring adapted to hold a bottom surface of a 2D woven composite specimen comprising a top surface and a bottom surface, at least a first set of fibers disposed in a first fiber direction and a second set of fibers disposed in a second fiber direction, the first and second set of fibers interlaced at an angle, and a loading ring, the support ring having a diameter greater than the loading ring, the loading ring disposed concentric to the support ring and configured to contact the center of the top surface of the 2D woven composite under conditions of monotonic force to induce biaxial flexure in the woven composite specimen;

a strain measurement device to obtain strain measurements during the inducement of biaxial flexure, whereby the strain measurements obtained are used to determine the equibiaxial compressive strength of the woven composite specimen, the strain measurement device comprising a first strain with a first strain gauge operatively connected to the bottom surface in a configuration that is parallel to the first fiber direction, and measuring a second strain with a second strain gauge operatively connected to the bottom surface in a configuration that is parallel to the second fiber direction.

36. The system of claim 35 wherein the diameter of the support ring is 3 to 5 times greater than the diameter of the loading ring.

* * * * *